United States Patent

Linsey

[11] 4,332,333
[45] Jun. 1, 1982

[54] PUNCTURE SPIKE HANDLE

[75] Inventor: Mark Linsey, Anaheim, Calif.

[73] Assignee: American Hospital Supply Corporation, Evanston, Ill.

[21] Appl. No.: 170,502

[22] Filed: Jul. 21, 1980

[51] Int. Cl.³ .............................................. B67B 7/24
[52] U.S. Cl. .................................. 222/83; 128/272.3; 222/479; D24/24
[58] Field of Search ................... 222/81, 83, 83.5, 85, 222/86, 88, 400.7, 475, 478, 479; 239/272, 309; 128/214 D, 214.2, 272, 272.2, 272.3; 141/329; D24/24, 25

[56] References Cited

U.S. PATENT DOCUMENTS

| D. 138,589 | 8/1944 | Brandenburg | D24/24 |
| D. 165,591 | 1/1952 | Lee | D24/25 |
| D. 169,237 | 4/1953 | Barrett et al. | D24/24 |
| 2,416,391 | 2/1947 | Hixson | 128/214 |
| 3,175,554 | 3/1965 | Stewart | D24/25 |
| 3,454,006 | 7/1969 | Langdon | D24/24 X |
| 3,581,423 | 5/1971 | Gilman | 222/81 |
| 3,941,171 | 3/1976 | Ogle | 128/272.3 X |
| 4,022,258 | 5/1977 | Steidley | 222/81 X |
| 4,057,060 | 11/1977 | Roth | 222/83 X |
| 4,150,669 | 4/1979 | Lattorre | 128/214.2 X |

Primary Examiner—Gil Weidenfeld
Assistant Examiner—Fred A. Silverberg
Attorney, Agent, or Firm—Roger A. Williams

[57] ABSTRACT

A handle for axial and rotational manipulation of a puncture spike for entering the closure of a medical liquid container or the like. The handle has a pair of opposed concave gripping surfaces that flair outwardly to provide a greater angle between the gripping surfaces adjacent their forward ends than adjacent their rearward ends. This handle construction improves the ease of manipulation during longitudinal puncture, as well as rotationally twisting the spike. Lateral protrusions on the handle at the forward ends of the gripping surfaces provide additional leverage when rotating the spike.

1 Claim, 4 Drawing Figures

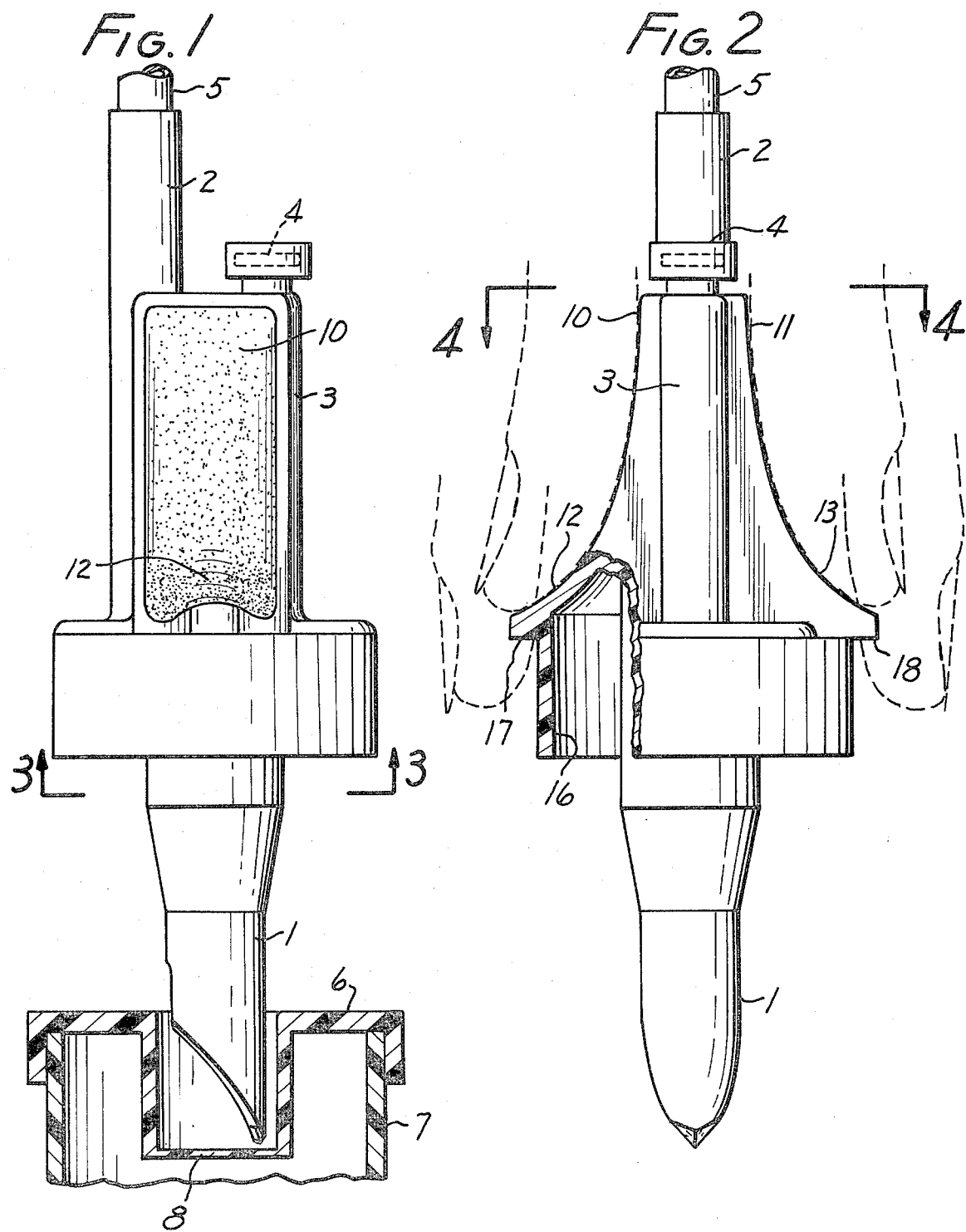

PUNCTURE SPIKE HANDLE

BACKGROUND

U.S. Pat. No. 4,022,258 describes a spike used to puncture the closure of a medical liquid container. Because these spikes are relatively large; i.e., approximately ½ inch in diameter, considerable axial force is needed to make the puncture. It should be recognized that the large diameter spikes, which are sold sterile and disposed of after a single use, are generally made of a thermoplastic material because of economics. Because of the spike's complexity, they cannot be conveniently made out of steel with precision ground, extremely sharp puncture tips.

Because of the very large axial force needed to initiate the puncture, the operator sometimes rotationally wiggles or twists the spike while applying axial pressure to initiate the puncture. This in effect helps to provide a slight boring effect with the spike. Because of this combined axial force and rotational force, the handle is very important in manipulating these large diameter spikes. In the past, transverse flat flanges such as in U.S. Pat. No. 4,022,258, provided a sufficient ledge to push against, but were sometimes uncomfortable to the thumb and finger of the operator. U.S. Pat. No. 2,416,391 describes another type of medical liquid bottle spike with an inverted bell-shaped filter housing. If this housing 29 were used as the axial pressure handle, its circular dimensions would not provide a good grip for rotating the spike during puncture. The thumb and forefinger could easily slip off the inverted bell-shaped housing 29.

SUMMARY OF THE INVENTION

The present invention overcomes the problems of medical liquid container puncturing spikes mentioned above. This invention includes a handle with a pair of opposed gripping surfaces which flair outwardly in a forwardly direction to provide a greater angle between the forward end portions of the gripping surfaces. The gripping surfaces are substantially flatter in a transverse direction than a circular path generated by rotating the handle about its longitudinal axis. This construction provides a handle that is easy and comfortable to both rotationally twist and longitudinally push at the time of puncture. Preferably, forward end portions of the gripping surface are on laterally protruding members that alternatively can be gripped for additional leverage in twisting the spike. This handle construction also provides for easier twisting retraction of the spike.

THE DRAWINGS

FIG. 1 is a side elevational view of the puncture spike's handle as the puncture spike is ready to pierce the closure of a medical liquid container or the like;

FIG. 2 is a rear elevational view, partially in section, of the puncture spike's handle showing alternate positions of gripping the handle;

DETAILED DESCRIPTION

Figure 3:
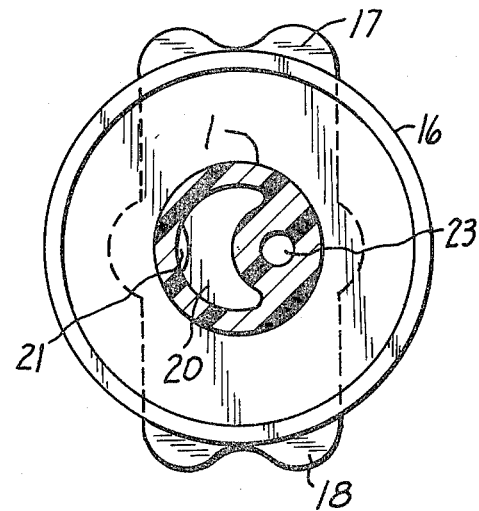
FIG. 3 is a sectional view taken along line 3—3 of FIG. 1.

In FIG. 1, a tubular puncture spike 1 is shown attached to a handle that includes an outlet tube 2 and an inlet tube 3. Inlet tube 3 is closed off by a filter member 4 that is pervious to air passage, but is impervious to liquid flow. The spike is used to puncture a closure 6 of a medical liquid container 7 by piercing a diaphragm 8. This diaphragm may be approximately ½ inch in diameter. Once the spike punctures the diaphragm 8 and is firmly seated in closure 6, the liquid container is inverted so that liquid can drain out of the container through puncture spike 1, outlet tube 2, and flexible conduit 5. Flexible conduit 5 can be connected to the internal surface of the outlet tube 2 (as shown), or can be connected to an external surface of outlet tube 2.

Because of the large size of the puncture spike 1 and the large diaphragm 8, considerable axial pressure is required on the handle of the puncture spike to make the puncture. This problem is further complicated because the puncture spikes of such large diameter are required for economic reasons to be made out of a thermoplastic material. Such thermoplastic spikes cannot maintain the very sharp and sturdy puncture points as the much smaller hypodermic "needles" made of precision ground stainless steel material. Due to the large axial force needed for puncture, a nurse or physician will often twistingly wiggle the spike while applying axial pressure to initiate the puncture. This motion can be uncomfortable to the thumb and forefinger of the nurse or physician when pushing against a simple lateral flange that is perpendicular to the longitudinal axis of the spike.

In FIG. 2, an improved handle construction is shown in which a pair of opposed gripping surfaces are approximately parallel at their rear end portions 10 and 11, but diverge and flair outwardly adjacent forward end portions 12 and 13. Preferably these diverging gripping surfaces are concave and roughly conform to the contour of the operator's thumb and forefinger. The gripping surfaces are on opposite sides of the outlet and inlet tubes 2 and 3. As seen in FIGS. 1 and 2, the gripping surfaces do not form a complete peripheral cone about the longitudinal axis of the spike. Instead, the concave surfaces are substantially flatter in a transverse direction than a circular path generated by rotating the handle about said longitudinal axis. Thus in FIG. 2 where the thumb and forefinger (shown in dotted line) are in the upper position, the generally transverse flat configuration of the gripping surfaces provide firm control when the puncture spike is rotationally twisted or wobbled. The diverging forward end portions 12 and 13, which preferably are separated by an angle greater than 90 degrees, provides firm control for longitudinal pushing on the spike. For this manipulation, the gripping surfaces preferably have a roughened texture. The handle configuration also aids in twistingly retracting the spike.

Figure 4:
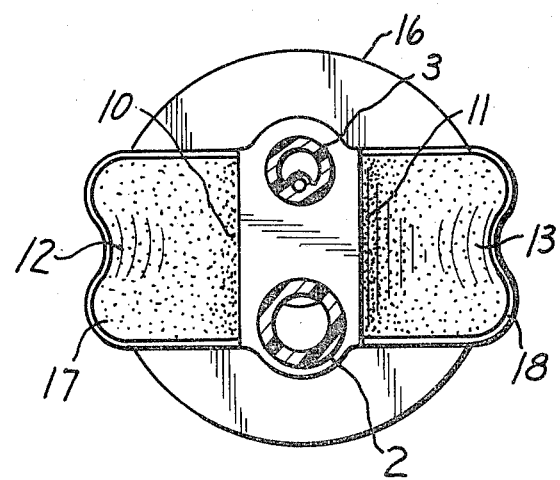
FIG. 4 is a sectional view taken along line 4—4 of FIG. 2.

The handle also includes a peripheral skirt 16 that extends forwardly along the handle to form a penetration stop when the skirt 16 contacts closure 6 of medical liquid container 7. Protruding members 17 and 18 adjacent this skirt form support for the forward end portions 12 and 13 of the gripping surfaces. The length of protruding members 17 and 18 are such that they do not interfere with the long fingernails of some operators. The protruding members are preferably concave, as shown in FIG. 4. Thus, when the thumb and forefinger (shown in dotted line) are in the lower position of FIG. 2, this provides an alternative gripping position for increased lever advantage in twisting the spike. The lower position shown in FIG. 2 is particularly applicable when twistingly removing the spike from its tight fit with the medical liquid container closure 6. The penetration stop skirt 16 insures the protruding members 17 and 18 are always spaced from container closure 6 to provide room for the thumb and forefinger at the lower position shown in FIG. 2. Skirt 16 also helps prevent touch contamination of the closure 6 with the operator's fingers.

As shown in FIG. 3, the position of protruding members 17 and 18 can readily be seen along with their relationship to skirt 16. The puncture spike 1 shown in FIG. 3 has a main lumen 20 for liquid drainage which communicates with a passage 21 of tube 2. A secondary lumen 23 communicates with air inletting tube 3.

FIG. 4 shows the view of the gripping surfaces from a rear of the handle. Here it can be seen that the gripping surfaces do not follow the complete peripheral or circular contour of the spike; i.e., they are substantially flatter in a transverse direction than a circular path generated by rotating the handle about its longitudinal axis. The gripping surfaces each extend less than one half way around the handle's transverse perimeter.

The spike of the present invention can be made of a thermoplastic material such as a styrene or acrylic type thermoplastic. Preferably, it is sold in a sterile condition and disposed of after a single use to avoid cross-contamination between hospital patients and the like.

In the foregoing description, a specific example has been used to describe the invention. However, it is understood by those skilled in the art that certain modifications can be made to this example without departing from the spirit and scope of the invention.

I claim:

1. A handle in combination with and for axial and rotational manipulation of a puncture spike that extends forwardly from the handle, said handle comprises: a body having a longitudinal axis and having a pair of passages extending longitudinally through the body and through the spike; a pair of opposed gripping surfaces; each of said gripping surfaces having a forward end and a rearward end and at least a portion that is substantially flatter in a transverse direction than a circular path generated by rotating the handle about said longitudinal axis; the gripping surfaces diverge outwardly in a forward direction to provide a greater angle between the gripping surfaces adjacent the forward ends than adjacent the rearward ends; wherein the gripping surfaces are generally concave in the longitudinal direction but are generally flat in a lateral direction, the gripping surfaces are approximately parallel adjacent their rearward ends and diverge outwardly by an angle greater than 90 degrees adjacent their forward ends, each of said gripping surfaces extends around less than one half of the handle's transverse perimeter and has a roughened texture; the handle has a penetration stop that extends beyond and is connected to forward end portions of the gripping surfaces, wherein the penetration stop is a skirt, said skirt having a top end portion and a bottom end portion; the bottom end portion of the spike engages an item being punctured, the skirt surrounds the puncture spike, the spike having a downstream end which extends outwardly from the skirt, the gripping surfaces have the forward end portions on laterally protruding members, the laterally protruding members having outer edges that are transversely concave for gripping to gain additional leverage for rotating the handle and the spike, the protruding members extend laterally outward from the skirt and are connected to the top end portion of the skirt and are spaced rearwardly from the bottom end portion so that the protruding members are always spaced from the item being punctured, the gripping surfaces are on opposite sides of the pair of passages extending through the body.

* * * * *